(12) United States Patent
Zhang et al.

(10) Patent No.: US 10,794,912 B2
(45) Date of Patent: Oct. 6, 2020

(54) IMMUNOADSORBENT FOR PURIFYING FIVE KINDS OF MYCOTOXINS INCLUDING FUMONISIN $B_1$ AND AFLATOXIN $B_1$, AND COMPLEX AFFINITY COLUMN

(71) Applicant: OILCROPS RESEARCH INSTITUTE OF CHINESE ACADAMY OF AGRICULTURE SCIENCES, Hubei (CN)

(72) Inventors: Zhaowei Zhang, Hubei (CN); Peiwu Li, Hubei (CN); Qi Zhang, Hubei (CN); Xiaofeng Hu, Hubei (CN); Wen Zhang, Hubei (CN)

(73) Assignee: OILCROPS RESEARCH INSTITUTE OF CHINESE ACADAMY OF AGRICULTURE SCIENCES, Hubei (CN)

( * ) Notice: Subject to any disclaimer, the term of this patent is extended or adjusted under 35 U.S.C. 154(b) by 171 days.

(21) Appl. No.: 15/915,011

(22) Filed: Mar. 7, 2018

(65) Prior Publication Data
US 2018/0259526 A1    Sep. 13, 2018

(30) Foreign Application Priority Data
Mar. 7, 2017 (CN) .......................... 2017 1 0134052

(51) Int. Cl.
| | | |
|---|---|---|
| *G01N 33/53* | (2006.01) | |
| *G01N 33/577* | (2006.01) | |
| *B01J 20/286* | (2006.01) | |
| *B01D 15/38* | (2006.01) | |
| *G01N 33/543* | (2006.01) | |

(52) U.S. Cl.
CPC ....... *G01N 33/577* (2013.01); *B01D 15/3804* (2013.01); *B01J 20/286* (2013.01); *G01N 33/543* (2013.01); *G01N 33/54366* (2013.01); *G01N 33/54393* (2013.01); *G01N 2333/37* (2013.01); *G01N 2333/38* (2013.01); *G01N 2333/385* (2013.01)

(58) Field of Classification Search
CPC .......... G01N 33/577; G01N 33/54393; G01N 33/543; G01N 33/54366; G01N 2333/38; G01N 2333/37; G01N 2333/385; G01N 30/02; G01N 33/53; B01D 15/3804; B01D 15/22; B01D 15/20; B01J 20/286
See application file for complete search history.

(56) References Cited

FOREIGN PATENT DOCUMENTS

| | | |
|---|---|---|
| CN | 102127523 | 7/2011 |
| CN | 103849604 | 6/2014 |
| CN | 104707362 | 6/2015 |

*Primary Examiner* — Carmencita M Belei
(74) *Attorney, Agent, or Firm* — JCIPRNET (57) ABSTRACT

An immunoadsorbent for purifying fumonisin $B_1$, aflatoxin $B_1$, ochratoxin A, zearalenone and sterigmatocystin; a complex affinity column and its preparation method; and a method for detecting the mycotoxins using the same are provided. The immunoadsorbent comprises a solid-phase support, and an anti-fumonisin $B_1$ monoclonal antibody, an anti-aflatoxin $B_1$ monoclonal antibody, an anti-ochratoxin A monoclonal antibody, an anti-zearalenone monoclonal antibody and an anti-sterigmatocystin monoclonal antibody which are coupled to the solid-phase support, wherein the anti-fumonisin $B_1$ monoclonal antibody is secreted by a hybridoma cell strain Fm7A11. The complex affinity column can be used for purification and detection of a fumonisin $B_1$ sample, an aflatoxin $B_1$ sample, an ochratoxin A sample, a zearalenone sample and a sterigmatocystin sample at the same time.

10 Claims, 1 Drawing Sheet

Specification includes a Sequence Listing.

# IMMUNOADSORBENT FOR PURIFYING FIVE KINDS OF MYCOTOXINS INCLUDING FUMONISIN B₁ AND AFLATOXIN B₁, AND COMPLEX AFFINITY COLUMN

CROSS-REFERENCE TO RELATED APPLICATION

This application claims the priority benefit of China application serial No. 201710134052.1, filed on Mar. 7, 2017. The entirety of the above-mentioned patent application is hereby incorporated by reference herein and made a part of this specification.

BACKGROUND OF THE INVENTION

1. Field of the Invention

The invention relates to an immunoadsorbent for purifying five kinds of mycotoxins including fumonisin $B_1$ and aflatoxin $B_1$, and a complex affinity column.

2. Description of Related Art

Fumonisins are the water-soluble metabolites produced by *Fusaria* at a certain temperature and humidity and are a kind of di-ester compounds with similar structures, composed of different polyhydric alcohols and tricarballylic acids. Fumonisins can interfere with the normal physiological functions of plants within a low concentration, are non-enzymatic compounds which have toxic effects on plant metabolism, and belong to mycotoxins and non-host specific toxins. Fumonisins are mainly distributed on such crops as corn, sorghum and wheat, and can cause seedlings blight, decay of roots, stems and seeds as well as other agricultural economic losses. Fumonisins can cause various specific toxicological effects on livestock and laboratory animals, such as leukoencephalomalacia in horses and rabbits. The symptoms are neurotoxicity, disturbance of consciousness, blindness and ataxia, and even death in some severe cases. Fumonisins can also cause pulmonary edema, hydrothorax, and injuries in the liver and esophagus of pigs. Fumonisins can also cause atherosclerosis in primates, hepatocyte apoptosis and nephrotoxicity in rats, lambs and calves, as well as having effect of liver toxicity and carcinogenic, causing serious economic losses to the livestock husbandry.

Aflatoxins are a group of secondary metabolites with similar structures produced by *Aspergillus flavus, Aspergillus parasiticus*, are a group of compounds with bi-furocoumarins as the basic structure, are widely distributed in cereals, feedstuffs and processed products thereof, and have the highest toxicity and the highest frequency of pollution among two hundred kinds of mycotoxins known at present. Aflatoxins have the effects of inducing mutation, inhibiting immunity and carcinogenesis. Aflatoxin $B_1$ ($AFB_1$) is the most toxic and carcinogenic. The main target organ on which $AFB_1$ acts is liver. $AFB_1$ is widely recognized as a cause of liver cancer. The liver of people who eat food containing a low level of aflatoxins on a long-term basis will also be damaged. The International Agency for Research on Cancer classified $AFB_1$ as Group 1 carcinogens.

Ochratoxins are mold nephrotoxins produced by *Aspergillus ochraceus* and *Penicillium verrucosum*. Ochratoxins can be divided into two types, ochratoxin A and ochratoxin B, among which ochratoxin A is more toxic. Ochratoxins with toxic concentrations can be produced by *Aspergillus ochraceus* at the temperature as low as 4. Animal taking 1 ppm of ochratoxin A on the basis of weight dose can die in 5-6 days. Common lesions are renal tubular epithelial damage and intestinal lymphoid necrosis. After feeding animals with a daily feed containing 1 ppm of ochratoxins on the basis of concentration for 3 months, polydipsia, frequent urination and slow growth of animals and decreased feed utilization can be caused. Kidney damage is detectable after feeding animals with a daily feed containing as little as 200 ppb of ochratoxins for weeks. Other clinical symptoms are diarrhea, anorexia and dehydration. Sometimes the clinical symptoms are not obvious, and in areas where ochratoxin poisoning is endemic, the only observable lesions of animals during slaughter are the pale and firm kidneys.

Zearalenone, also known as F-2 toxin, is first isolated from maize with gibberellic disease. The toxigenic bacteria of zearalenone are mainly *Fusarium* strains such as *Fusarium graminearum* and *Fusarium tricinctum*. Zearalenone mainly contaminates maize, wheat, rice, barley, millet, oats and other cereals, among which the positive detection rate of maize is 45%, and the maximum toxic amount can reach 2909 mg/kg. The detection rate of wheat is 20%, and the toxic amount is 0.364-11.05 mg/kg. Zearalenone has high heat resistance, and can only be completely destroyed after being treated at 110° C. for 1 h. Zearalenone has the effects of estrogen, mainly acts on the reproductive system, and can cause estrogen hyperfunction in livestock, poultry and laboratory mice. Gestational animals (including humans) consuming foods containing zearalenone can cause miscarriage, stillbirth and fetal malformation. Various foods made of flour from wheat with gibberellic disease can also cause symptoms of central nervous system poisoning, such as nausea, chills, headaches, mental depression and ataxia.

Sterigmatocystin (ST) is a mycotoxin, and is mainly a secondary metabolite produced by fungi such as *Aspergillus versicolor, Aspergillus flavus, Aspergillus nidulans* and *Aspergillus rugulosus*. Sterigmatocystin is widely present in nature. In addition to being metabolically produced in *Aspergillus versicolor, Aspergillus flavus* and *Aspergillus nidulans*, sterigmatocystin also widely exists in other molds such as *Aspergillus chevalieri, Aspergillus ruber, Aspergillus ustus, Aspergillus amstelodami, Aspergillus quadrilineatus, Aspergillus variecolor* and *Aspergillus unguis, Chaetomium, Aspergillus aurantio-bruneus* and the like. Sterigmatocystin was first isolated from the mycelium of *aspergillus versicolor* and named by Japanese scholar Yuichi Hatsuda, but did not attract the attention of people at that time. The outbreak of the "turkey X-disease" in the United Kingdom in 1960 was proven that the outbreak was resulted from aflatoxin poisoning, and only since then people started to pay attention on ST which is similar to aflatoxins in structure. In recent years, incidents of chicken, cows, sheep, horses and other livestock in the United Kingdom, Canada, the United States and China die from acute poisoning due to ingestion of ST-containing feed are observed. Animal experiments show that ST can cause liver cancer and lung cancer in animals.

At present, the detection methods of mycotoxins such as fumonisin $B_1$, aflatoxin $B_1$, ochratoxin A, zearalenone and sterigmatocystin are mainly thin-layer chromatography, enzyme-linked immunosorbent assay (ELISA), immunoaffinity chromatography-liquid chromatography, and immunoaffinity chromatography-fluorescence spectrophotometry. Thin-layer chromatography requires contact with a large number of standards, is not good for the health of experimenters, and is low in sensitivity. ELISA is only suitable for qualitative detection, and is prone to false positives and false negatives. Immunoaffinity chromatography-liquid chromatography can quantitatively detect the content of fumonisin $B_1$, aflatoxin $B_1$, ochratoxin A, zearalenone and sterigmatocystin in many commercial products. Due to the adoption of advanced biotechnologies, the method can detect the content of fumonisin $B_1$, aflatoxin $B_1$, ochratoxin A, zearalenone and sterigmatocystin without the use of toxic solvents such as chloroform and dichloromethane. Therefore, it is imperative to prepare a stable immunoaffinity column and establish an economical, fast, accurate and safe test method.

SUMMARY OF THE INVENTION

In order to solve the problem in the prior art that an immunoaffinity column with stable performance for detecting fumonisin $B_1$ ($FB_1$), aflatoxin $B_1$ ($AFB_1$), ochratoxin A (OTA), zearalenone (ZEN) and sterigmatocystin (ST) is needed, the present invention provides an immunoadsorbent for purifying fumonisin $B_1$, aflatoxin $B_1$, ochratoxin A, zearalenone and sterigmatocystin, a complex affinity column and a preparation method and application of the complex affinity column.

In order to achieve the above object, the technical scheme adopted by the present invention is:

an immunoadsorbent for purifying fumonisin $B_1$, aflatoxin $B_1$, ochratoxin A, zearalenone and sterigmatocystin comprises a solid-phase support, and an anti-fumonisin $B_1$ monoclonal antibody, an anti-aflatoxin $B_1$ monoclonal antibody, an anti-ochratoxin A monoclonal antibody, an anti-zearalenone monoclonal antibody and an anti-sterigmatocystin monoclonal antibody which are coupled to the solid-phase support, wherein the anti-fumonisin $B_1$ monoclonal antibody is a monoclonal antibody secreted by a hybridoma cell strain Fm7A11 with a deposit number of CCTCC No. C201636, and the hybridoma cell strain Fm7A11 has been preserved at China Center for Type Culture Collection (CCTCC), Wuhan University, Wuhan, China in Mar. 29, 2016 with a deposit number of CCTCC No. C201636.

According to the scheme, the solid-phase support is a sepharose.

A complex affinity column loaded with the immunoadsorbent for purifying fumonisin $B_1$, aflatoxin $B_1$, ochratoxin A, zearalenone and sterigmatocystin.

The complex affinity column for purifying fumonisin $B_1$, aflatoxin $B_1$, ochratoxin A, zearalenone and sterigmatocystin is prepared by the following steps:

(a) preparation of matrix a CNBr-activated sepharose matrix powder is subjected to washing by HCl at pH 2-3 to remove impurities to obtain a CNBr-activated sepharose matrix;

wherein CNBr-activated sepharose is provided in a lyophilized form, and the additives are washed away with HCl before being coupled to a target ligand at a low pH (pH 2-3) condition;

(b) Ligand coupling each of the anti-fumonisin $B_1$ monoclonal antibody, the anti-aflatoxin $B_1$ monoclonal antibody, the anti-ochratoxin A monoclonal antibody, the anti-zearalenone monoclonal antibody and the anti-sterigmatocystin monoclonal antibody for coupling are dissolved in a coupling buffer to obtain a monoclonal antibody solution, the CNBr-activated sepharose matrix in the step (a) is rapidly transferred to the monoclonal antibody solution to obtain a mixture, and the mixture is thoroughly mixed for 2-4 h at room temperature (20-25° C.);

(c) Ligand blocking to block all remaining active sites;

(d) removal of uncoupled ligands after the ligand blocking in the step (c); and (e) column packing.

According to the scheme, the concentration of HCl for the washing in the step (a) is 1 mmol/L and the washing time is 15 min.

According to the scheme, the coupling buffer in the step (b) is 0.2 mol/L $NaHCO_3$, the pH is 8.3, and the concentration of each of the monoclonal antibody is 10-15 mg/mL.

According to the scheme, the ligand block of the step (c) is conducted by transferring the treated CNBr-activated sepharose matrix treated in the step (b) to a 0.1 mol/L Tris-HCl buffer, and then keep it standing for 2-4 h at room temperature.

According to the scheme, the step (d) is conducted by washing the treated CNBr-activated sepharose matrix treated in the step (c) with a buffer of pH 4 and a buffer of pH 8 in sequence for at least 3 cycles, wherein the buffer of pH 4 is a 0.1 mol/L acetate/sodium acetate buffer with pH of 4, and the buffer of pH 8 is a 0.1 mol/L Tris-HCl buffer with pH of 8.

According to the scheme, the step (e) is conducted by washing with 0.01% $NaN_3$-PBS with 5 times the volume of the CNBr-activated sepharose matrix in step (d), performing storing with the 0.01% $NaN_3$-PBS, and then packing the column.

In the scheme, the anti-ochratoxin A antibody may be a monoclonal antibody secreted by a hybridoma cell strain 1H2 with a deposit number of CCTCC No. C201329. The anti-zearalenone antibody may be a monoclonal antibody secreted by a hybridoma cell strain 2D3 with a deposit number of CCTCC No. C201328. The anti-sterigrnatocystin antibody may be a monoclonal antibody secreted by a hybridoma cell strain ST03 with a deposit number of CCTCC No. C2013187.

The anti-aflatoxin $B_1$ monoclonal antibody may be a monoclonal antibody secreted by a hybridoma cell strain 3G1 with a deposit number of CCTCC No. C201014.

The anti-aflatoxin $B_1$ monoclonal antibody can be replaced by an anti-aflatoxin general monoclonal antibody. Aflatoxin $B_1$, aflatoxin $B_2$, aflatoxin $G_1$ and aflatoxin $G_2$ can be simultaneously purified by selecting the anti-aflatoxin general monoclonal antibody, and on this basis, co-detection of aflatoxin $B_1$, aflatoxin $B_2$, aflatoxins $G_1$ and aflatoxin $G_2$ can be achieved.

On this basis, a purification-liquid chromatography-mass spectrometry method for detecting the content of fumonisin $B_1$, aflatoxin $B_1$, ochratoxin A, zearalenone and sterigmatocystin by means of the immunoaffinity column is established, when a sample containing fumonisin $B_1$, aflatoxin, ochratoxin A, zearalenone and sterigmatocystin passes through the complex affinity column, the immunoadsorbent specifically adsorbs fumonisin $B_1$, aflatoxin, ochratoxin A, zearalenone and sterigmatocystin, other impurities are flowed out from the complex affinity column, then the complex affinity column is eluted with chromatography-grade methanol, fumonisin $B_1$, aflatoxin $B_1$, ochratoxin A, zearalenone and sterigmatocystin are eluted from the column, the flow rate for elution can be 1-2 mL/min, and an eluate, namely the purified and concentrated sample is collected to be detected by a high performance liquid chromatography-mass spectrometer, thereby obtaining the content of the multiple toxins.

A method for detecting the content of fumonisin $B_1$, aflatoxin $B_1$, ochratoxin A, zearalenone and sterigmatocystin based on the complex affinity column is provided, when a sample containing fumonisin $B_1$, aflatoxin, ochratoxin A, zearalenone and sterigmatocystin passes through the immunoaffinity column, the immunoadsorbent specifically adsorbs fumonisin $B_1$, aflatoxin, ochratoxin A, zearalenone and sterigmatocystin, other impurities flow out of the immunoaffinity column, then the affinity column is eluted with chromatography-grade methanol, and an eluate, namely the purified and concentrated sample is collected to be detected by a high performance liquid chromatography-mass spectrometer, thereby obtaining the content of the multiple toxins.

The conditions of the high performance liquid chromatography-mass spectrometer:
a. mobile phase: A, 0.05% formic acid/water solution; B, 0.05% formic acid/acetonitrile solution
b. gradient elution: 15%-50% B for 0-3 min; 4-5 min, 50%-70% B for 4-5 min; 70%-100% B for 6.5-8 min; 100%-50% B for 8-10 min; 50%-15% B for 10-11 min; and 15% B for 11-15 min.
c. chromatographic column: C-18 column
d. flow rate: 200 µL/min; and
e. the mass spectrometry scanning parameters for various toxins are shown in Table 1.

TABLE 1

Scanning parameters for various toxins

| Toxin | Precursor ion (m/z) | Quantitative daughter ions (m/z) | Cone voltage (V) | Collision energy (V) |
|---|---|---|---|---|
| $AFB_1$ | 313.0 $[M + H]^+$ | 241.0 285.0 284.9 | 30 | 35 35 27 |
| OTA | 402.0 $[M - H]^-$ | 166.8 358.1 | 30 | 30 20 |
| ZEN | 317.0 $[M - H]^-$ | 130.8 174.9 305.2 | 30 | 30 25 30 |
| ST | 325.2 $[M + H]^+$ | 115.2 310.1 | 30 | 64 24 |
| $FB_1$ | 722.05 $[M + H]^+$ | 334.0 352.0 265.0 | 30 | 35 35 25 |

The specific quantitative method can be as follows:

a standard working solution containing different concentrations of fumonisin $B_1$, aflatoxin $B_1$, ochratoxin A, zearalenone and sterigmatocystin is drawn by a sample injector to be injected into a high performance liquid chromatography-mass spectrometer, high performance liquid chromatogram-mass spectrograms of various toxins and the standard solution peak area of each toxin are obtained under the conditions separately, a standard curve of various toxins is drawn, and an external standard method is used to calculate the content of each toxin.

According to the scheme, the flow rate for elution is 1-2 mL/min.

The affinity column prepared by the method of the present invention can be used for high performance liquid chromatography-mass spectrometry detection of fumonisin $B_1$, aflatoxin $B_1$, ochratoxin A, zearalenone and sterigmatocystin and has stable performance. By using the affinity column, an economical, fast, accurate and safe detection method is established, which can be used for the purification of five toxin samples simultaneously without any interference among the five kinds of toxins.

BRIEF DESCRIPTION OF THE DRAWINGS

FIG. 1 shows the mass spectrogram-chromatograms of fumonisin $B_1$ ($FB_1$), aflatoxin $B_1$ ($AFB_1$), ochratoxin A (OTA), zearalenone (ZEN) and sterigmatocystin (ST) in a sample; and from top to bottom the sequence is sterigmatocystin, zearalenone, ochratoxin A, fumonisin $B_1$, aflatoxin $B_1$.

DESCRIPTION OF THE EMBODIMENTS

Embodiment 1

Figure 1:
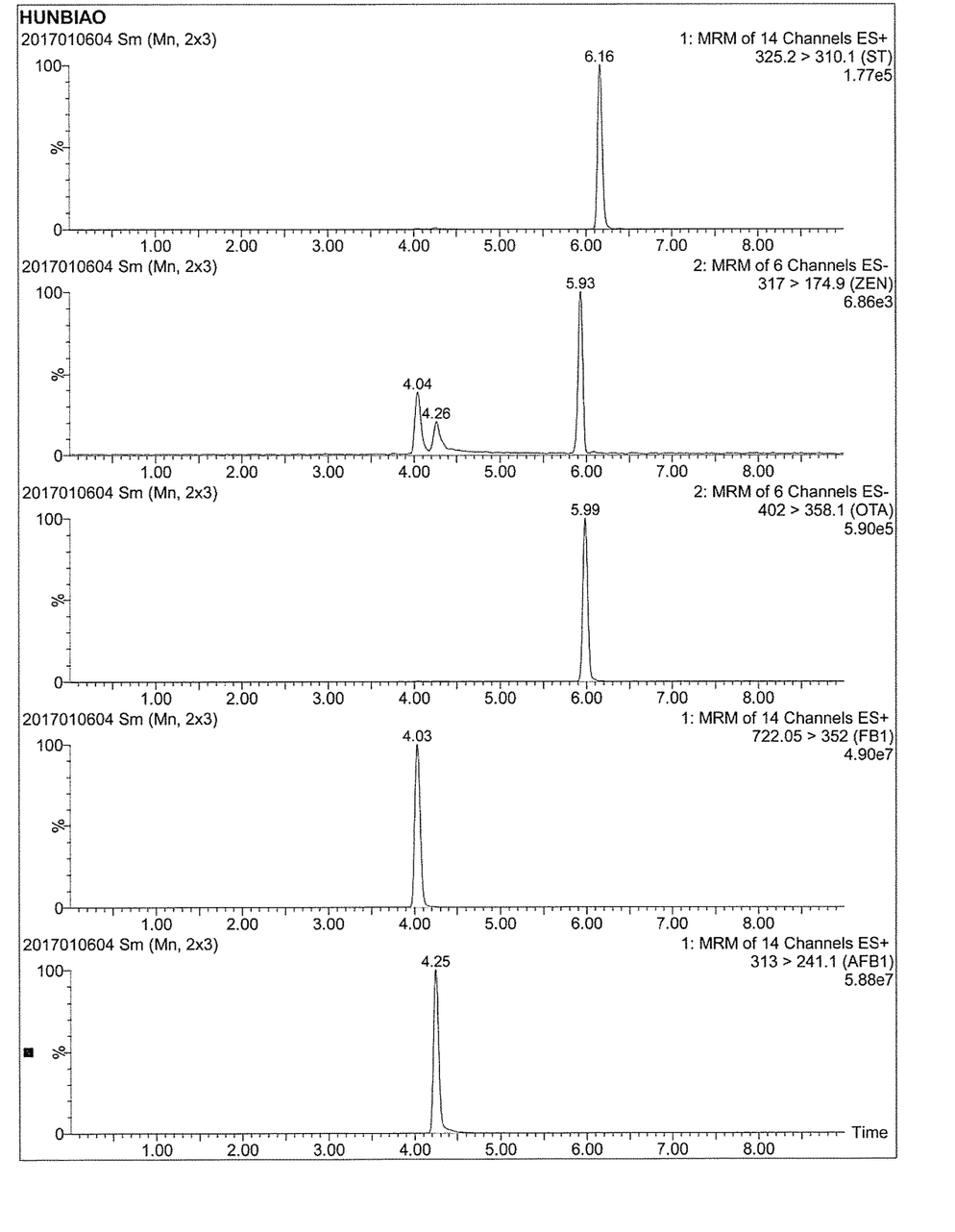

Example 1: Acquisition of an Anti-Aflatoxin $B_1$ Monoclonal Antibody

An aflatoxin general monoclonal antibody is secreted by a hybridoma cell strain 3G1 with a deposit number of CCTCC No. C201014, and is prepared in advance according to the method reported in the patent number ZL201210117614.9. The preparation method comprises the steps of injecting the obtained hybridoma cell strain 3G1 into a BALB/c mouse previously treated with a Freund's incomplete adjuvant, collecting the ascites of the mouse and conducting purification to obtain the anti-aflatoxin $B_1$ monoclonal antibody. The purification method is an octanoic acid-ammonium sulfate method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 30-35 µL, the mixture is mixed at room temperature for 30-60 min and stands at 4° C. for more than 2 h, then centrifugation is conducted at 4° C. and 12000 r/min for more than 30 min, a precipitate is discarded, a resulting supernatant is filtered through double-layer filter paper, a phosphate buffer with 1/10 filtrate volume and with a molar concentration of 0.1 mol/L and a pH of 7.4 is added, the pH of the mixed liquid is adjusted with 2 mol/L sodium hydroxide solution to 7.4, precooling is conducted at 4° C., ammonium sulfate is slowly added till the final concentration of ammonium sulfate reaches 0.277 g/mL, the mixture stands at 4° C. for more than 2 h, then centrifugation is conducted at 4° C. and 12000 r/min for more than 30 min, a supernatant is discarded, a resulting precipitate is resuspended with 0.01 mol/L phosphate buffer of 1/10 original volume of ascites, placed in a dialysis bag and dialyzed with pure water, the well-dialyzed protein solution is frozen in a −70° C. freezer and then lyophilized with a freezing vacuum dryer, lyophilized powder is collected, thus obtaining the purified anti-aflatoxin $B_1$ monoclonal antibody, and the antibody is stored in a −20° C. refrigerator for use; and the acetate buffer is obtained by adding water to 0.29 g of sodium acetate and 0.141 mL of acetic acid to 100 mL; and the 0.1 mol/L phosphate buffer is obtained by adding water to 0.8 g of sodium chloride, 0.29 g of sodium phosphate dibasic dodecahydrate, 0.02 g of potassium chloride and 0.02 g of potassium dihydrogen phosphate to 100 mL.

Example 2: Acquisition of Anti-Ochratoxin A Monoclonal Antibody

An anti-ochratoxin A monoclonal antibody is secreted by a hybridoma cell strain 1H2 with a deposit number of CCTCC No. C201329, and is prepared in advance according to the method reported in the patent number 201310115921.8. The preparation method comprises the steps of injecting the hybridoma cell strain 1H2 into the abdomen of a BALB/c mouse previously treated with a Freund's incomplete adjuvant, collecting the ascites of the mouse and conducting purification to obtain the anti-ochratoxin A monoclonal antibody. The purification method is an octanoic acid-ammonium sulfate method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 30-35 µL, the mixture is mixed at room temperature for 30-60 min and stands at 4° C. for more than 2 h, then centrifugation is conducted at 4° C. and 12000 r/min for more than 30 min, a precipitate is discarded, a resulting supernatant is filtered through double-layer filter paper, a phosphate buffer with 1/10 filtrate volume and with a molar concentration of 0.1 mol/L and a pH of 7.4 is added, the pH of the mixed liquid is adjusted with 2 mol/L sodium hydroxide solution to 7.4, precooling is conducted at 4° C., ammonium sulfate is slowly added till the final concentration of ammonium sulfate reaches 0.277 g/mL, the mixture stands at 4° C. for more than 2 h, then centrifugation is conducted at 4° C. and 12000 r/min for more than 30 min, a supernatant is discarded, a resulting precipitate is resuspended with 0.01 mol/L phosphate buffer of 1/10 original volume of ascites with a pH of 7.4, placed in a dialysis bag and dialyzed with pure water, the well-dialyzed protein solution is frozen in a −70° C. freezer and then lyophilized with a freezing vacuum dryer, lyophilized powder is collected, thus obtaining the purified anit-ochratoxin A monoclonal antibody, and the antibody is stored in a −20° C. refrigerator for use; and the acetate buffer is obtained by adding water to 0.29 g of sodium acetate and 0.141 mL of acetic acid to 100 mL; the 0.01 mol/L phosphate buffer is obtained by adding water to 0.8 g of sodium chloride, 0.29 g of sodium phosphate dibasic dodecahydrate, 0.02 g of potassium chloride and 0.02 g of potassium dihydrogen phosphate to 100 mL; and the 0.1 mol/L phosphate buffer is obtained by adding water to 8 g of sodium chloride, 2.9 g of sodium phosphate dibasic dodecahydrate, 0.2 g of potassium chloride and 0.2 g of potassium dihydrogen phosphate to 100 mL.

Example 3: Acquisition of Anti-Zearalenone Monoclonal Antibody

An anti-zearalenone monoclonal antibody is secreted by a hybridoma cell strain 2D3 with a deposit number of CCTCC No. C201328, and is prepared in advance according to the method reported in the patent number 201310115825.3. The preparation method comprises the steps of injecting the hybridoma cell strain 2D3 into the abdomen of a BALB/c mouse previously treated with a Freund's incomplete adjuvant, collecting the ascites of the mouse and conducting purification to obtain the anti-zearalenone monoclonal antibody. The purification method is an octanoic acid-ammonium sulfate method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 30-35 µL, the mixture is mixed at room temperature for 30-60 min and stands at 4° C. for more than 2 h, then centrifugation is conducted at 4° C. and 12000 r/min for more than 30 min, a precipitate is discarded, a resulting supernatant is filtered through double-layer filter paper, a phosphate buffer with 1/10 filtrate volume and with a molar concentration of 0.1 mol/L and a pH of 7.4 is added, the pH of the mixed liquid is adjusted with 2 mol/L sodium hydroxide solution to 7.4, precooling is conducted at 4° C., ammonium sulfate is slowly added till the final concentration of ammonium sulfate reaches 0.277 g/mL, the mixture stands at 4° C. for more than 2 h, then centrifugation is conducted at 4° C. and 12000 r/min for more than 30 min, a supernatant is discarded, a resulting precipitate is resuspended with 0.01 mol/L phosphate buffer of 1/10 original volume of ascites with a pH of 7.4, placed in a dialysis bag and dialyzed with pure water, the well-dialyzed protein solution is frozen in a −70° C. freezer and then lyophilized with a freezing vacuum dryer, lyophilized powder is collected, thus obtaining the purified anti-zearalenone monoclonal antibody, and the antibody is stored in a −20° C. refrigerator for use; and the acetate buffer is obtained by adding water to 0.29 g of sodium acetate and 0.141 mL of acetic acid to 100 mL; the 0.01 mol/L phosphate buffer is obtained by adding water to 0.8 g of sodium chloride, 0.29 g of sodium phosphate dibasic dodecahydrate, 0.02 g of potassium chloride and 0.02 g of potassium dihydrogen phosphate to 100 mL; and the 0.1 mol/L phosphate buffer is obtained by adding water to 8 g of sodium chloride, 2.9 g of sodium phosphate dibasic dodecahydrate, 0.2 g of potassium chloride and 0.2 g of potassium dihydrogen phosphate to 100 mL.

Example 4: Acquisition of Anti-Sterigmatocystin Monoclonal Antibody

An anti-sterigmatocystin monoclonal antibody is secreted by a hybridoma cell strain ST03 with a deposit number of CCTCC No. C2013187, and is prepared in advance according to the method reported in the patent number 201410115952.8. The preparation method comprises the steps of injecting the obtained hybridoma cell strain ST03 into the abdomen of a BALB/c mouse previously treated with a Freund's incomplete adjuvant, collecting the ascites of the mouse and conducting purification to obtain the anti-sterigmatocystin monoclonal antibody. The purification method is an octanoic acid-ammonium sulfate purification method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 33 µL, the mixture is mixed at room temperature for 30-60 min and stands at 4° C. for more than 2 h, then centrifugation is conducted at 4° C. and 12000 r/min for more than 30 min, a precipitate is discarded, a resulting supernatant is filtered through double-layer filter paper, a phosphate buffer with 1/10 filtrate volume and with a molar concentration of 0.1 mol/L and a pH of 7.4 is added, the pH of the mixed liquid is adjusted with 2 mol/L sodium hydroxide solution to 7.4, precooling is conducted at 4° C., ammonium sulfate is slowly added till the final concentration of ammonium sulfate reaches 0.277 g/mL, the mixture stands at 4° C. for more than 2 h, then centrifugation is conducted at 4° C. and 12000 r/min for more than 30 min, a supernatant is discarded, a resulting precipitate is resuspended with 0.01 mol/L phosphate buffer of 1/10 original volume of ascites, placed in a dialysis bag and dialyzed with pure water, the well-dialyzed protein solution is frozen in a −70° C. freezer and then lyophilized with a freezing vacuum dryer, lyophilized powder is collected, thus obtaining the purified anit-sterigmatocystin monoclonal antibody, and the antibody is stored in a −20° C. refrigerator for use; and the acetate buffer is obtained by adding water to 0.29 g of sodium acetate and 0.141 mL of acetic acid to 100 mL; and the 0.1 mol/L phosphate buffer is obtained by adding water to 0.8 g of sodium chloride, 0.29 g of sodium phosphate dibasic dodecahydrate, 0.02 g of potassium chloride and 0.02 g of potassium dihydrogen phosphate to 100 mL.

Example 5 Acquisition of Anti-Fumonisin $B_1$ Monoclonal Antibody

Screening of Hybridoma Cell Strain Fm7A11

1. Antigen Synthesis and Animal Immunization

Commercially available fumonisin $B_1$ standards are purchased for complete antigen synthesis as follows: 2 mg of $FB_1$ standard powder and 2 mg of EDC are dissolved in 500 μL of a 0.01 mol/L PBS solution respectively to obtain an EDC solution and an $FB_1$ solution, and 4 mg/mL (0.01 mol/L PBS solution) EDC solution is added dropwise to the solubilized $FB_1$ solution and gently agitated for 10 min at room temperature. 5 mg/mL of (0.01 mol/L PBS solution) BSA solution is added dropwise to the mixed liquid, and the mixture is stirred at room temperature and reacts for 4 h. Dialysis is conducted for 3 days. Finally, conventional UV scanning identification is conducted, and an identification result shows that $FB_1$-BSA complete antigen preparation succeeds.

Six 6-week-old BALB/c mice are purchased and immunized with a fumonisin complete antigen $FB_1$-BSA synthesized in the laboratory. During the first time of immunization, the fumonisin complete antigen and an equal volume of Freund's complete adjuvant are emulsified and then injected subcutaneously into multiple points of the nape of the mice. The second time of immunization is carried out three weeks later. A Freund's incomplete adjuvant and an equal volume of fumonisin complete antigen are emulsified and then injected subcutaneously into multiple points of the nape of the mice. The third time of immunization and the fourth time of immunization are conducted two weeks after the last time of immunization separately, in the same immunization manner as the second time of immunization. The same dose is adopted for four times of immunization, 100 μg per mouse only. On the 7th day after the third time of immunization, blood is collected from the caudal vein of the mice and serum is separated. The serum titer of the mice is monitored through indirect ELISA, the sensitivity of the serum of the mice is measured through indirect competitive ELISA, a mouse corresponding to the serum with higher titer and sensitivity is selected for the final booster immunization, and the immune dose is 2 times the previous dose.

2. Cell Fusion

Three days after the final booster immunization, cell fusion is carried out with a conventional method using 50% (by weight) polyethylene glycol, namely PEG (molecular weight being 1450) as a fusion agent. Specifically, under an aseptic condition, the mice to be fused are killed by breaking the neck, spleen cells are isolated and mixed with murine myeloma cells SP2/0 at a ratio of 5:1, and the mixed cells are washed with an RPMI-1640 basal medium and centrifuged at 1200 rpm for 5 min. A supernatant is discarded, draining is conducted, 1 mL of PEG is added for fusion of 1 min, the RPMI-1640 basal medium is slowly added, centrifugation is conducted, a supernatant is discarded, a precipitation is fusion cells, resuspension is conducted with 20 mL of complete medium, suspended cells are added to 80 mL of semi-solid medium, and the mixture is added to a 6-well cell culture plate after uniform mixing at 2 mL/well, and then placed in a 37° C. $CO_2$ incubator for culture.

The cell complete medium containing 1% HAT contains 20% (by volume) of fetal calf serum, 75% (by volume) of RPMI-1640 basal medium, 1% (by weight) of L-glutamine, 1% (by volume) of HEPES, 1% (by volume) of double antibody (10,000 units per milliliter of penicillin and 10,000 micrograms per milliliter of streptomycin), 2% (by volume) of growth factor (HFCS) and 1% (by weight) of hypoxanthine-aminopterin-thymidine (HAT) and methylcellulose, the above components are purchased from Sigma-Aldrich Co. Ltd.

3. Cell Strain Screening and Cloning

Two to three weeks after cell fusion, when cell colonies grow to be visible, clones are picked out from the culture medium with a micropipette and transferred to a 96-well cell culture plate to be cultured with HAT liquid, and a culture supernatant is drawn for testing when the cells grow to the position of ⅔ of the well bottom. A two-step screening method is adopted. Indirect ELISA is adopted in the first step to screen out positive wells resistant to fumonisin but not resistant to carrier protein BSA; indirect competitive ELISA is adopted in the second step to detect the positive wells screened out in the first step, fumonisin $B_1$ is used as a competitive antigen, wells with higher absorbance and sensitivity are chosen (higher absorbance means a higher final measured value for a well with a competitive antigen of 0, namely a positive control well, and higher sensitivity means a smaller competitive antigen concentration, namely $IC_{50}$ value when the suppression rate is 50%), subcloning is conducted with a limiting dilution method, then the same two-step method is adopted for detection after the subcloning, and subcloning is conducted in the same manner for 4-5 times to obtain a hybridoma cell strain Fm7A11.

4. Anti-Fumonisin $B_1$ Monoclonal Antibody Hybridoma Cell Strain Fm7A11 Antibody Variable Region Sequence Determination (1) Total RNA extraction: total RNA capable of producing the hybridoma cell strain Fm7A11 is extracted by using a total RNA extraction kit from TIANGEN according to the instruction manual;

(2) Synthesis of cDNA: a first strand of cDNA is synthesized by reverse transcription according to a SuperScript™-2II reverse transcriptase instruction manual with the total RNA obtained in the step 1 as a template and oligo(dT)15 as a primer, and the primer oligo(dT)15 is purchased from Invitrogen; and (3) Cloning of variable region genes by PCR: primers are designed according to the conserved sites of mouse antibody gene sequences in GENBANK, to amplify the antibody heavy chain and light chain variable region genes with cDNA as a template. PCR procedures: 94° C. 30 s, 58° C. 45 s, 72° C. 1 min, amplification of 30 cycles, final extension for 10 min at 72° C. After PCR products are subjected to electrophoretic separation by 1% (by weight) sepharose, DNA fragments are purified and recovered with a kit and ligated into a support pMD18-T to be transformed into *Escherichia coli* DH5a competent cells, and positive clones are picked out and sent to Shanghai Sunny Biotechnology Co., Ltd. for sequencing. The sequences of the primers are as follows: the sequences of the forward and reverse primers for the heavy chain variable region are 5'-CAG GTS MAR CTG MAG GAG TCW G-3' (22mer, SEQ ID NO: 5) and 5'-CAG GGG CCA GTG GAT AGA CAG ATG GGG G-3' (28mer, SEQ ID NO: 6), respectively, wherein S, M, R and W are merging bases, M=A/C, R=A/G, S=G/C, W=A/T, and the sequences of the forward and reverse primers for the light chain variable region are 5'-GAC ATC AAG ATG ACC CAG TCT CCA-3' (24mer, SEQ ID NO: 7) and 5'-CCG TTT TAT TTC CAG CTT GGT CCC-3' (24mer, SEQ ID NO: 8), respectively.

The obtained gene sequence results: the length of the coding gene sequence of the heavy chain variable region is 379 bp, the sequence is shown in SEQ ID NO: 1, it is deduced from the obtained gene sequence that the heavy chain variable region coded by the gene sequence is composed of 126 amino acids, and the sequence is shown in SEQ ID NO: 3; and the length of the coding gene sequence of the light chain variable region is 348 bp, the sequence is shown in SEQ ID NO: 2, it is deduced from the obtained gene sequence that the light chain variable region coded by the gene sequence is composed of 116 amino acids, and the sequence is shown in SEQ ID NO: 4.

5. Preparation and Purification, Subtypes and Characterization of Anti-Fumonisin $B_1$ Monoclonal Antibody The anti-fumonisin $B_1$ monoclonal antibody hybridoma cell strain Fm7A11 obtained in Example 1 is injected into a BALB/c mouse previously treated with a Freund's incomplete adjuvant, the ascites of the mouse is collected, and the antibody is purified with an octanoic acid-ammonium sulfate method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 30-35 μL, and the mixture is mixed at room temperature for 30-60 min and stands at 4° C. for more than 2 h. Then centrifugation is conducted at 4° C. and 12000 r/min for more than 30 min, a precipitate is discarded, a resulting supernatant is filtered through double-layer filter paper, a phosphate buffer with ⅒ filtrate volume and with a molar concentration of 0.1 mol/L and a pH of 7.4 is added, the pH of the mixed liquid is adjusted with 2 mol/L sodium hydroxide solution to 7.4, ammonium sulfate is slowly added in an ice bath till the final concentration of ammonium sulfate reaches 0.277 g/mL, the mixture stands at 4° C. for more than 2 h, then centrifugation is conducted at 4° C. and 12000 r/min for more than 30 min, a supernatant is discarded, a resulting precipitate is resuspended with 0.01 mol/L phosphate buffer of ⅒ original volume of ascites with a pH of 7.4, placed in a dialysis bag and dialyzed with 0.01 mol/L PBS for two days, then dialysis is conducted with PB for two days, a protein solution in the dialysis bag is taken out and centrifuged, a supernatant is collected, a precipitate is discarded, and then the product is pre-frozen at −70° C. and then lyophilized in a lyophilizer. Lyophilized powder is collected, thus obtaining the purified anti-fumonisin $B_1$ monoclonal antibody;

the acetate buffer is obtained by adding water to 0.29 g of sodium acetate and 0.141 mL of acetic acid to 100 mL; the 0.01 mol/L phosphate buffer is obtained by adding water to 0.8 g of sodium chloride, 0.29 g of sodium phosphate dibasic dodecahydrate, 0.02 g of potassium chloride and 0.02 g of potassium dihydrogen phosphate to 100 mL; and the 0.1 mol/L phosphate buffer is obtained by adding water to 8 g of sodium chloride, 2.9 g of sodium phosphate dibasic dodecahydrate, 0.2 g of potassium chloride and 0.2 g of potassium dihydrogen phosphate to 100 mL.

The subtype of the anti-fumonisin $B_1$ monoclonal antibody secreted by the hybridoma cell strain Fm7A11 is identified as IgG2b by using a commercially available subtype identification kit.

The titer of the antibody obtained by purifying the ascites of the mouse is measured to be $3.2 \times 10^5$ through conventional non-competitive enzyme-linked immunosorbent assay (ELISA), that is to say, a solution measurement result is positive when the antibody is diluted by $3.2 \times 10^5$ times. The sensitivity to fumonisin $B_1$ is measured to be 0.32 ng/mL through conventional indirect competitive ELISA. The cross-reactivities to fumonisins $B_2$ and $B_3$ are 4.3% and 12.8%. Cross-reactivities with aflatoxin, zearalenone, T-2 toxin, ochratoxin and vomitoxin are all less than 0.1%.

Embodiment 2

Preparation of Fumonisin $B_1$, Aflatoxin $B_1$, Ochratoxin A, Zearalenone and Sterigmatocystin Complex Immunoaffinity Column 1. Preparation of Matrix 1 g of sepharose lyophilized matrix powder required (3.5 mL of swelling matrix of final volume can be obtained from per gram of lyophilized matrix powder) is weighed and the sepharose lyophilized matrix powder is dissolved in 1 mmol/L HCl. The matrix will swell immediately and is then placed in a sintered glass filter to be washed with 1 mmol/L HCl for 15 min.

2. Ligand (Antibody) Coupling a. The anti-fumonisin $B_1$ monoclonal antibody, the anti-aflatoxin $B_1$ monoclonal antibody, the anti-ochratoxin A monoclonal antibody, the anti-zearalenone monoclonal antibody and the anti-sterigmatocystin monoclonal antibody for coupling are dissolved by using a coupling buffer of 0.2 mol/L $NaHCO_3$ with a pH of 8.3, wherein the concentration of each antibody is 12.5 mg/mL, and the dissolved antibodies are placed in an ice bath for temporary storage. The antibody-containing coupling buffer is added to a capped container capable of being completely sealed. CNBr activated sepharose is rapidly transferred to the antibody solution. The mixture is thoroughly mixed for 2-4 h at the room temperature (20-25° C.).

b. Calculation of the coupling rate: centrifugation is conducted at 2,000 rpm till sepharose is centrifuged to the bottom of a tube, a supernatant is transferred to a new centrifuge tube, and the protein content of the supernatant is measured. The coupling rate is calculated to be 98.5% (indicating that coupling is successful). The sepharose centrifuged to the bottom of the tube is taken out and washed with the coupling buffer to remove excess ligands.

c. Block: the matrix is transferred to a 0.1 mol/L Tris-HCl buffer. The matrix in the 0.1 mol/L Tris-HCl buffer stands for 2-4 h at room temperature to block all remaining active sites.

d. In order to remove uncoupled unwanted ligands after coupling, the matrix is washed with buffers with a pH of 4 and a pH of 8, namely, 0.1 mol/L acetate/sodium acetate buffer and 0.1 mol/L Tris-HCl buffer in sequence for at least 3 cycles, wherein the usage amount of each buffer is at least 5 times the volume of the matrix. Each washing cycle comprises the steps of conducting washing with the 0.1 mol/L acetate/sodium acetate buffer first and then with the 0.1 mol/L Tris-HCl buffer.

e. Washing is conducted with 5 times the colloidal volume of 0.01% $NaN_3$-PBS and storage is conducted with 0.01% $NaN_3$-PBS.

3. Column loading: a slurry is prepared by combining with and using the buffer, and 75% of sedimenting matrix and 25% of phosphate buffer (pH 7.0) are mixed; the slurry is poured into the column continuously; a glass rod leaning against the inner wall of the column is used for column packing, which will help reduce the generation of air bubbles; after column packing, an opening in the lower end of the affinity column is closed and a top part of the affinity column is taken down; the remaining portion of the affinity column is carefully filled with a PBS buffer with a pH of 7.0 to form an upward meniscus at the top end of the affinity column; a top sieve plate is inserted into the affinity column at a certain angle to ensure that there is no air under the sieve 
plate; the sieve plate is locked at a proper position of the surface of the matrix, an opening in the bottom of the affinity column is opened, 0.01% $NaN_3$-PBS for sterile filtration with 5 times column bed volume passes through the column, and storage is conducted with 0.01% $NaN_3$-PBS, thereby completing loading and balancing of the fumonisin $B_1$, aflatoxin $B_1$, ochratoxin A, zearalenone and sterigmatocystin affinity column so that the affinity column can be directly used.

Embodiment 3: Detection of Fumonisin $B_1$, Aflatoxin $B_1$, Ochratoxin A, Zearalenone and Sterigmatocystin in Rice 1.0 Detection of Fumonisin $B_1$, Aflatoxin $B_1$, Ochratoxin a, Zearalenone and Sterigmatocystin in Rice Rice adding recovery experiments: fumonisin $B_1$ with the concentration gradient of 500 μg/kg, 1000 μg/kg and 2000 μg/kg, and aflatoxin $B_1$, ochratoxin A, zearalenone and sterigmatocystin with the concentration gradients of 10 μg/kg, 20 μg/kg and 50 μg/kg are added respectively. Five groups of parallel tests are made for each experiment.

Three Gradients:

The dose for the first experiment: 500 μg/kg of fumonisin $B_1$, 10 μg/kg of aflatoxin $B_1$, 10 μg/kg of ochratoxin A, 10 μg/kg of zearalenone and 10 μg/kg of sterigmatocystin.

The dose for the second experiment: 1000 μg/kg of fumonisin $B_1$, 20 μg/kg of aflatoxin $B_1$, 20 μg/kg of ochratoxin A, 20 μg/kg of zearalenone and 20 μg/kg of sterigmatocystin.

The dose for the third experiment: 2000 μg/kg of fumonisin $B_1$, 50 μg/kg of aflatoxin $B_1$, 50 μg/kg of ochratoxin A, 50 μg/kg of zearalenone and 50 μg/kg of sterigmatocystin.

Extraction of fumonisin $B_1$, aflatoxin $B_1$, ochratoxin A, zearalenone and sterigmatocystin in rice:

20.0 g of ground sample (particle size being less than 2 mm) is weighed accurately in a homogenizer, 100 mL of acetonitrile/water/formic acid (80+18+2) is added, and homogenization, high-speed stirring and extraction are conducted for 2 min. Quantitative filter paper filtration: 5.0 mL of filtrate is accurately transferred, 15.0 mL of PBS solution with a PH of 7.0 is added for dilution, and filtration is conducted with glass fiber filter paper for 1-2 times till filtrate becomes clear. The complex immunoaffinity column is attached to the bottom of a 10.0 mL glass syringe. 10.0 mL of sample extract is accurately transferred into the glass syringe, an air pressure pump and the glass syringe are connected, and the pressure is adjusted to enable the solution to slowly pass through the complex immunoaffinity column at a flow rate of about 6 mL/min until 2-3 mL of air passes through the column. The column is eluted twice with 10.0 mL of water, all eluate is discarded, and 2-3 mL of air is made to pass through the column. 1.0 mL of chromatography-grade methanol is accurately added for elution, the flow rate is 1-2 mL/min, and all eluate is collected in a glass test tube for testing.

2.0 High Performance Liquid Chromatography-Mass Spectrometry Conditions a. Mobile phase: A, 0.05% formic acid/water solution; B, 0.05% formic acid/acetonitrile solution b. Gradient elution: 0-3 min, 15%-50% B; 4-5 min, 50%-70% B; 6.5-8 min, 70%-100% B; 8-10 min, 100%-50% B; 10-11 min, 50%-15% B; and 11-15 min, 15% B.

c. Chromatographic column: C-18 column (column length 50 mm, inner diameter 2.1 mm, packing diameter 1.7 μm)

d. Flow rate: 200 μL/min and e. The mass spectrometry scanning parameters for various toxins are shown in Table 1.

3.0 Quantification

A standard working solution containing different concentrations of fumonisin $B_1$, aflatoxin $B_1$, ochratoxin A, zearalenone and sterigmatocystin is drawn by a sample injector to be injected into a high performance liquid chromatography-mass spectrometer, high performance liquid chromatogram-mass spectrograms of various toxins and the standard solution peak area of each toxin are obtained under the conditions separately, a standard curve of each toxin is drawn, and an external standard method is used to calculate the content of each toxin.

4.0 Results

The results of the adding standard recovery for rice are between 85%-105% with RSD less than 10%. The results show that the method completely meets the analysis requirement for detecting fumonisin $B_1$, aflatoxin $B_1$, ochratoxin A, zearalenone and sterigmatocystin in rice. The results are shown in Table 1-Table 5 respectively.

TABLE 1

Recovery results of fumonisin $B_1$ in rice

| Spiked concentration of fumonisin $B_1$ μg/kg | Recovery rate 1 % | Recovery rate 2 % | Recovery rate 3 % | Recovery rate 4 % | Recovery rate 5 % | RSD % |
|---|---|---|---|---|---|---|
| 500 | 104.1 | 99.3 | 101.3 | 99.5 | 96.7 | 2.7 |
| 1000 | 86.8 | 92.3 | 86.4 | 87.5 | 98.3 | 5.6 |
| 2000 | 93.5 | 104.6 | 86.7 | 97.7 | 92.5 | 7.0 |

TABLE 2

Recovery results of aflatoxin $B_1$ in rice

| Spiked concentration of aflatoxin $B_1$ μg/kg | Recovery rate 1 % | Recovery rate 2 % | Recovery rate 3 % | Recovery rate 4 % | Recovery rate 5 % | RSD % |
|---|---|---|---|---|---|---|
| 10 | 98.6 | 90.9 | 91.5 | 86.7 | 100.5 | 6.1 |
| 20 | 103.4 | 93.3 | 87.6 | 87.6 | 90.6 | 7.1 |
| 50 | 87.6 | 101.1 | 98.4 | 93.5 | 102.4 | 6.3 |

TABLE 3

Recovery results of ochratoxin A in rice

| Spiked concentration of ochratoxin A μg/kg | Recovery rate 1 % | Recovery rate 2 % | Recovery rate 3 % | Recovery rate 4 % | Recovery rate 5 % | RSD % |
|---|---|---|---|---|---|---|
| 10 | 92.5 | 91.2 | 87.7 | 103.1 | 98.8 | 6.5 |
| 20 | 88.4 | 91.1 | 100.9 | 92.3 | 86.9 | 5.9 |
| 50 | 95.6 | 103.4 | 96.8 | 102.2 | 98.4 | 3.4 |

TABLE 4

Recovery results of zearalenone in rice

| Spiked concentration of zearalenone μg/kg | Recovery rate 1 % | Recovery rate 2 % | Recovery rate 3 % | Recovery rate 4 % | Recovery rate 5 % | RSD % |
|---|---|---|---|---|---|---|
| 10 | 88.8 | 90.6 | 95.5 | 97.6 | 102.7 | 5.9 |
| 20 | 90.4 | 93.8 | 85.6 | 94.4 | 100.8 | 6.0 |
| 50 | 103.6 | 100.7 | 89.7 | 88.8 | 98.6 | 6.9 |

TABLE 5

Recovery results of sterigmatocystin in rice

| Spiked concentration of sterigmatocystin μg/kg | Recovery rate 1 % | Recovery rate 2 % | Recovery rate 3 % | Recovery rate 4 % | Recovery rate 5 % | RSD % |
|---|---|---|---|---|---|---|
| 10 | 100.8 | 100.2 | 92.7 | 99.6 | 95.4 | 3.6 |
| 20 | 93.3 | 99.9 | 101.6 | 99.7 | 103.5 | 3.9 |
| 50 | 89.7 | 94.4 | 96.6 | 102.5 | 93.2 | 5.0 |

Embodiment 4: Detection of Fumonisin $B_1$, Aflatoxin $B_1$, Ochratoxin A, Zearalenone and Sterigmatocystin in Edible Oil 1.0 Detection of Fumonisin $B_1$, Aflatoxin $B_1$, Ochratoxin A, Zearalenone and Sterigmatocystin in Edible Oil Edible oil adding standard recovery experiments: fumonisin $B_1$ with the concentration gradient of 500 μg/kg, 1000 μg/kg and 2000 μg/kg, and aflatoxin $B_1$, ochratoxin A, zearalenone and sterigmatocystin with the concentration gradients of 10 μg/kg, 20 μg/kg and 50 μg/kg are added respectively. Five groups of parallel tests are made for each experiment.

Extraction of fumonisin $B_1$, aflatoxin $B_1$, ochratoxin A, zearalenone and sterigmatocystin in edible oil:

vegetable oil liquid sample extraction: 5.0 g of vegetable oil sample is weighed accurately in a 50 mL centrifuge tube, 15.0 mL of 70% aqueous methanol is added, oscillation blending is conducted in a vortex mixer for 2 min, centrifugation is conducted at 5000 r/min for 2 min, 10.0 mL of methanol solution layer is transferred, dilution is conducted with 20.0 mL of water, uniform mixing is conducted in a mixer, and filtration is conducted with glass fiber filter paper till filtrate becomes clear. The complex immunoaffinity column is attached to the bottom of a 10.0 mL glass syringe. 10.0 mL of sample extract is accurately transferred into the glass syringe, an air pressure pump and the glass syringe are connected, and the pressure is adjusted to enable the solution to slowly pass through the complex immunoaffinity column at a flow rate of about 6 mL/min until 2-3 mL of air passes through the column. The column is eluted twice with 10.0 mL of water, all eluate is discarded, and 2-3 mL of air is made to pass through the column. 1.0 mL of chromatography-grade methanol is accurately added for elution, the flow rate is 1-2 mL/min, and all eluate is collected in a glass test tube for testing.

2.0 High Performance Liquid Chromatography-Mass Spectrometry Conditions a. Mobile phase: A, 0.05% formic acid/water solution; B, 0.05% formic acid/acetonitrile solution b. Gradient elution: 0-3 min, 15%-50% B; 4-5 min, 50%-70% B; 6.5-8 min, 70%-100% B; 8-10 min, 100%-50% B; 10-11 min, 50%-15% B; and 11-15 min, 15% B.

c. Chromatographic column: C-18 column (column length 50 mm, inner diameter 2.1 mm, packing diameter 1.7 μm)

d. Flow rate: 200 μL/min and e. The mass spectrometry scanning parameters for various toxins are shown in Table 1.

3.0 Quantification

A standard working solution containing different concentrations of fumonisin $B_1$, aflatoxin $B_1$, ochratoxin A, zearalenone and sterigmatocystin is drawn by a sample injector to be injected into a high performance liquid chromatography-mass spectrometer, high performance liquid chromatogram-mass spectrograms of various toxins and the standard solution peak area of each toxin are obtained under the conditions separately, a standard curve of each toxin is drawn, and an external standard method is used to calculate the content of each toxin.

4.0 Results

The results of the adding recovery for vegetable oil are between 85%-105% with RSD less than 10%. The results show that the method completely meets the analysis requirement for detecting fumonisin $B_1$, aflatoxin $B_1$, ochratoxin A, zearalenone and sterigmatocystin in edible oil. The results are shown in Table 6-Table 10 respectively.

TABLE 6

Recovery results of fumonisin $B_1$ in vegetable oil

| Spiked concentration of fumonisin $B_1$ μg/kg | Recovery rate 1 % | Recovery rate 2 % | Recovery rate 3 % | Recovery rate 4 % | Recovery rate 5 % | RSD % |
| --- | --- | --- | --- | --- | --- | --- |
| 500 | 92.3 | 91.6 | 101.5 | 88.3 | 97.2 | 5.5 |
| 1000 | 104.1 | 103.4 | 92.8 | 90.8 | 93.4 | 6.5 |
| 2000 | 97.5 | 85.8 | 97.5 | 91.7 | 100.5 | 6.2 |

TABLE 7

Recovery results of aflatoxin $B_1$ in vegetable oil

| Spiked concentration of aflatoxin $B_1$ μg/kg | Recovery rate 1 % | Recovery rate 2 % | Recovery rate 3 % | Recovery rate 4 % | Recovery rate 5 % | RSD % |
| --- | --- | --- | --- | --- | --- | --- |
| 10 | 90.5 | 103.2 | 103.1 | 89.7 | 95.3 | 6.8 |
| 20 | 90.6 | 102.1 | 94.8 | 99.8 | 89.4 | 5.8 |
| 50 | 98.1 | 88.5 | 101.1 | 102.5 | 90.6 | 6.5 |

TABLE 8

Recovery results of ochratoxin A in vegetable oil

| Spiked concentration of ochratoxin A μg/kg | Recovery rate 1 % | Recovery rate 2 % | Recovery rate 3 % | Recovery rate 4 % | Recovery rate 5 % | RSD % |
| --- | --- | --- | --- | --- | --- | --- |
| 10 | 87.2 | 102.5 | 91.8 | 90.1 | 96.9 | 6.5 |
| 20 | 89.8 | 94.4 | 99.7 | 90.6 | 89.1 | 4.8 |
| 50 | 87.7 | 91.6 | 98.7 | 89.3 | 102.2 | 6.7 |

TABLE 9

Recovery results of zearalenone in vegetable oil

| Spiked concentration of zearalenone μg/kg | Recovery rate 1 % | Recovery rate 2 % | Recovery rate 3 % | Recovery rate 4 % | Recovery rate 5 % | RSD % |
| --- | --- | --- | --- | --- | --- | --- |
| 10 | 96.5 | 103.1 | 85.8 | 86.3 | 102.2 | 8.8 |
| 20 | 88.4 | 89.1 | 91 | 99.5 | 102.1 | 6.7 |
| 50 | 102.5 | 105.7 | 101.8 | 102.2 | 89.9 | 6.1 |

TABLE 10

Recovery results of sterigmatocystin in vegetable oil

| Spiked concentration of sterigmatocystin μg/kg | Recovery rate 1 % | Recovery rate 2 % | Recovery rate 3 % | Recovery rate 4 % | Recovery rate 5 % | RSD % |
| --- | --- | --- | --- | --- | --- | --- |
| 10 | 97.3 | 96.7 | 94.9 | 87.9 | 86.7 | 5.4 |
| 20 | 90.5 | 99.1 | 103.1 | 89.7 | 95.6 | 5.9 |
| 50 | 94.7 | 90.5 | 99.4 | 103.3 | 104.4 | 5.9 |

What is claimed is:

1. An immunoadsorbent for purifying fumonisin $B_1$, aflatoxin $B_1$, ochratoxin A, zearalenone and sterigmatocystin, comprising
a solid-phase support; and
an anti-fumonisin $B_1$ monoclonal antibody, an anti-aflatoxin $B_1$ monoclonal antibody, an anti-ochratoxin A monoclonal antibody, an anti-zearalenone monoclonal antibody and an anti-sterigmatocystin monoclonal antibody, wherein each antibody is coupled to the solid-phase support,
wherein the anti-fumonisin $B_1$ monoclonal antibody is secreted by a hybridoma cell strain Fm7A11, and the hybridoma cell strain Fm7A11 preserved in China Center for Type Culture Collection, Wuhan University, Wuhan, China on Mar. 29, 2016 with the deposit number CCTCC No. C201636.

2. The immunoadsorbent according to claim 1, wherein the solid-phase support is a sepharose.

3. A complex affinity column for purifying fumonisin $B_1$, aflatoxin $B_1$, ochratoxin A, zearalenone and sterigmatocystin, comprising the immunosorbent of claim 1, wherein the immunosorbent of claim 1 is loaded on a column to form the complex affinity column.

4. A preparation method of the complex affinity column of claim 3, comprising the following steps:
(a) preparing a CNBr-activated sepharose matrix by washing a CNBr-activated sepharose matrix powder with a washing solution comprising HCl at pH 2-3, to remove impurities;
(b) forming an antibody solution comprising mixing each of the monoclonal antibodies of claim 1 with a coupling buffer;
(c) forming a sepharose immunosorbent comprising mixing the CNBr-activated sepharose matrix of (a) with the antibody solution of (b) for 2-4 h at room temperature (20-25° C.) to couple each of the monoclonal antibodies onto the CNBr-activated sepharose matrix;
(d) blocking all remaining active sites on the CNBr-activated sepharose matrix of (c);
(e) washing the sepharose immunosorbent of (d) to remove uncoupled antibodies; and
(f) packing a column with the sepharose immunosorbent of (e).

5. The preparation method according to claim 4, wherein concentration of the HCl for the washing in the step (a) is 1 mmol/L and the washing time is 15 min.

6. The preparation method according to claim 4, wherein the coupling buffer in the step (b) is 0.2 mol/L $NaHCO_3$, pH 8.3, and concentration of each of the monoclonal antibody is 10-15 mg/mL.

7. The preparation method according to claim 4, wherein the blocking of (d) is conducted by transferring the treated CNBr-activated sepharose matrix of (c) to a 0.1 mol/L Tris-HCl buffer, and incubate for 2-4 h at room temperature.

8. The preparation method according to claim 4, wherein the washing of (e) is conducted by washing the sepharose immunosorbent of (d) with a buffer of pH 4 and a buffer of pH 8 in sequence for at least 3 cycles, wherein the buffer of pH 4 is a 0.1 mol/L acetate/sodium acetate buffer with pH of 4, and the buffer of pH 8 is a 0.1 mol/L Tris-HCl buffer with pH of 8.

9. The preparation method according to claim 4, wherein the packing of (f) is conducted by washing with 0.01% $NaN_3$-PBS with 5 times volume of the CNBr-activated sepharose matrix, storing with the 0.01% $NaN_3$-PBS, and then packing the column.

10. A method for detecting content of fumonisin $B_1$, aflatoxin $B_1$, ochratoxin A, zearalenone and sterigmatocystin with the complex affinity column according to claim 3, comprising
1. pretreating a sample to obtain a sample extract;
2. purifying and concentrating fumonisin $B_1$, aflatoxin $B_1$, ochratoxin A, zearalenone and sterigmatocystin in the sample, comprising
   a. providing the complex affinity column comprising the immunosorbent according to claim 3, wherein the immunosorbent specifically binds fumonisin $B_1$, aflatoxin $B_1$, ochratoxin A, zearalenone and sterigmatocystin;
   b. loading the sample extract onto the complex affinity column to absorb fumonisin $B_1$, aflatoxin $B_1$, ochratoxin A, zearalenone and sterigmatocystin;
   c. washing the column to remove impurities; and
   d. eluting fumonisin $B_1$, aflatoxin $B_1$, ochratoxin A, zearalenone and sterigmatocystin from the column with chromatography-grade methanol; and
3. detecting fumonisin $B_1$, aflatoxin $B_1$, ochratoxin A, zearalenone and sterigmatocystin in an eluate of the eluting of 2d by a high performance liquid chromatography-mass spectrometer.

\* \* \* \* \*

SEQUENCE LISTING

<160> NUMBER OF SEQ ID NOS: 8

<210> SEQ ID NO 1
<211> LENGTH: 379
<212> TYPE: DNA
<213> ORGANISM: Mus musculus

<400> SEQUENCE: 1
caggtgcagc tgaaggagtc aggacctggc ctggtggcgc cctcacagag cctgtccatc    60
acttgcactg tctctgggct ttcattaacc agctatggtg tacactgggt tcgtcaggcc   120
ccaggaaagg gtctggagtg gctgggagta atttggggtg gtggaaacac aaattataat   180
tcggctctca tgtccagact gagcatcagc aaagacaact ccaggagcca agttttctta   240
agaatgaaca gtctgcaaat tgatgacaca gccatgtact attgtgccag aggcaggatg   300
gactactggg gtcaaggaac ctcagtcacc gtctcgtcag ccaaaacgac acccccatct   360
gtctatccac tggcccctg                                                379

<210> SEQ ID NO 2
<211> LENGTH: 348
<212> TYPE: DNA
<213> ORGANISM: Mus musculus

<400> SEQUENCE: 2
gacatcaaga tgacccagtc tccatcttcc atgtatgcat ctctaggaga aagagtcact    60
atcacttgca aggcgagtca ggacattagt agctatttag ctggttaca gcagaaacca   120 gggaaatctc ctaagaccct gatctatcgt gcaaacacat tggtagaagg ggtcccatcc   180
agattcagtg gcagtggatc tggggaagat tattctctca ccatcagcag cctggagtat   240
gaagatatgg gaatttatta ttgtctacag tatgatgagt ttccgtacac gttcggaggg   300
gggaccaagc tggaaataaa acgggctgat gctgcaccaa ctgtatcc                348

<210> SEQ ID NO 3
<211> LENGTH: 126
<212> TYPE: PRT
<213> ORGANISM: Mus musculus

<400> SEQUENCE: 3

Gln Val Gln Leu Lys Glu Ser Gly Pro Gly Leu Val Ala Pro Ser Gln
1               5                   10                  15

Ser Leu Ser Ile Thr Cys Thr Val Ser Gly Leu Ser Leu Thr Ser Tyr
            20                  25                  30

Gly Val His Trp Val Arg Gln Ala Pro Gly Lys Gly Leu Glu Trp Leu
        35                  40                  45

Gly Val Ile Trp Gly Gly Gly Asn Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Ile Asp Asp Thr Ala Met Tyr Tyr Cys Ala
                85                  90                  95

Arg Gly Arg Met Asp Tyr Trp Gly Gln Gly Thr Ser Val Thr Val Ser
            100                 105                 110

Ser Ala Lys Thr Thr Pro Pro Ser Val Tyr Pro Leu Ala Pro
        115                 120                 125

<210> SEQ ID NO 4
<211> LENGTH: 116

<212> TYPE: PRT
<213> ORGANISM: Mus musculus

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Ser Ser Tyr
            20                  25                  30

Leu Gly Trp Leu Gln Gln Lys Pro Gly Lys Ser Pro Lys Thr Leu Ile
        35                  40                  45

Tyr Arg Ala Asn Thr Leu Val Glu Gly Val Pro Ser Arg Phe Ser Gly
    50                  55                  60

Ser Gly Ser Gly Glu Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 5
<211> LENGTH: 22
<212> TYPE: DNA
<213> ORGANISM: Artificial Sequence
<220> FEATURE:
<223> OTHER INFORMATION: Forward primer for the heavy chain variable
      region

<400> SEQUENCE: 5
caggtsmarc tgmaggagtc wg                                          22

<210> SEQ ID NO 6
<211> LENGTH: 28
<212> TYPE: DNA
<213> ORGANISM: Artificial Sequence
<220> FEATURE:
<223> OTHER INFORMATION: Reverse primer for the heavy chain variable
      region

<400> SEQUENCE: 6 cagggggccag tggatagaca gatgggggg                                  28

<210> SEQ ID NO 7
<211> LENGTH: 24
<212> TYPE: DNA
<213> ORGANISM: Artificial Sequence
<220> FEATURE:
<223> OTHER INFORMATION: Forward primer for the light chain variable
      region

<400> SEQUENCE: 7
gacatcaaga tgacccagtc tcca                                        24

<210> SEQ ID NO 8
<211> LENGTH: 24
<212> TYPE: DNA
<213> ORGANISM: Artificial Sequence

```
<220> FEATURE:
<223> OTHER INFORMATION: Reverse primer for the light chain variable
      region

<400> SEQUENCE: 8
ccgttttatt tccagcttgg tccc                                          24
```